US006659985B2

(12) United States Patent
Connor

(10) Patent No.: US 6,659,985 B2
(45) Date of Patent: Dec. 9, 2003

(54) METHOD TO USE TRANSDERMAL ADMINISTRATION OF ANDROGENS TO THE ADNEXA OF THE EYE

(75) Inventor: Charles Gerald Connor, Germantown, TN (US)

(73) Assignee: Southern College of Optometry, Memphis, TN (US)

( * ) Notice: Subject to any disclaimer, the term of this patent is extended or adjusted under 35 U.S.C. 154(b) by 0 days.

(21) Appl. No.: 10/060,554

(22) Filed: Jan. 30, 2002

(65) Prior Publication Data

US 2003/0144635 A1 Jul. 31, 2003

(51) Int. Cl.[7] .............................................. A61M 35/00
(52) U.S. Cl. ....................................... 604/294; 514/912
(58) Field of Search ......................... 604/289, 294–302; 514/912–915

(56) References Cited

U.S. PATENT DOCUMENTS

| | | | |
|---|---|---|---|
| 4,783,450 A | 11/1988 | Fawzi et al. .................. 514/78 |
| 4,978,532 A | 12/1990 | El-Rashidy ................. 424/448 |
| 5,041,434 A | 8/1991 | Lubkin ....................... 514/182 |
| 5,578,586 A | * 11/1996 | Glonek et al. ................ 514/76 |
| 5,620,921 A | 4/1997 | Sullivan ..................... 514/178 |
| 5,639,743 A | 6/1997 | Kaswan et al. ............. 514/171 |
| 5,869,090 A | 2/1999 | Rosenbaum ................ 424/449 |
| 5,888,493 A | 3/1999 | Sawaya ................... 424/78.04 |
| 6,048,846 A | 4/2000 | Cochran .................... 514/168 |
| 6,060,546 A | 5/2000 | Powell et al. .............. 524/267 |
| 6,093,706 A | 7/2000 | Zeligs ........................ 514/171 |
| 6,096,733 A | 8/2000 | Lubkin ....................... 514/182 |
| 6,107,289 A | 8/2000 | Sullivan ..................... 514/178 |
| 6,200,593 B1 | 3/2001 | Place ......................... 424/435 |
| 6,221,389 B1 | 4/2001 | Cannell et al. ............. 424/450 |
| 6,225,299 B1 | 5/2001 | Golbs et al. ................ 514/170 |
| 6,254,893 B1 | 7/2001 | MacKeen ................... 424/602 |
| 6,277,855 B1 | 8/2001 | Yerxa ......................... 514/256 |
| 6,284,263 B1 | 9/2001 | Place ......................... 424/435 |

FOREIGN PATENT DOCUMENTS

WO   WO 94/04155   3/1994

OTHER PUBLICATIONS

Handbook of Ocular Disease Managment; *Keratitis Sicca/Dry Eye Syndrome*.
Worda et al.; "Treatment of Keratoconjunctivitis Sicca with Topical Androgen" Maturitas 37 (2001) 209–212; published Jan. 13, 2001.
Tsubota, Kazuo "Tear Dynamics and Dry Eye," Department of Ophthalmology, Toyoko Dental College, Chiba, Japan and Department of Ophthalmology Keio University School of Medicine, Tokyo, Japan.
Sullivan et al. "Androgen Influence on the Meibomian Gland," Investigative Ophthalmology and Vision Science (2000).
Sullivan, et al. "Are Women with Sjogren's Syndrome Androgen Deficient?" Investigative Ophthalmology and Visions Science (2000).
Connor, et al. "A Weak Androgenic Artificial Tear Solution Decreases the Osmolarity of Dry Eye Patients," Investigative Opthalmology and Vision Science (2001).

(List continued on next page.)

*Primary Examiner*—Weilun Lo
*Assistant Examiner*—Michael Bogart
(74) *Attorney, Agent, or Firm*—Butler Snow, et al.

(57) ABSTRACT

This invention relates to a method for treating dry eye or increasing contact lens wear time through the transdermal delivery of androgenic hormones to the adnexa of the eye. More specifically, an androgenic hormone such as testosterone or dehydroepiandrosterone is solubilized in pharmaceutically effective carrier such as a facial cream or gel. The androgenic hormone in a pharmaceutically effective carrier is applied to the adnexa of the eye, which is the tissue adjacent to and surrounding the eyeball.

15 Claims, 1 Drawing Sheet

OTHER PUBLICATIONS

Bacman et al. "MuscarinicAcetylocholine Receptor Antibodies as a New Marker of Dry Eye Sjogren Syndrome." Investigative Ophthalomology and Vision Science (2001).

Connor et al. "The Efficacy of Androgenic Artificial Tears in the Treatment of Dry Eye," Optometry & Vision Science, Dec. 2001.

* cited by examiner

The Effect of Androgenic Cream on CL Wear Time

METHOD TO USE TRANSDERMAL ADMINISTRATION OF ANDROGENS TO THE ADNEXA OF THE EYE

FIELD OF THE INVENTION

This invention relates to a method to use transdermal administration of androgens. More specifically, this invention involves the transdermal delivery of androgenic hormones to the adnexa of the eye for the treatment of dry eye disease. Additionally, this invention relates to a method to increase contact lens wear time through the transdermal delivery of androgenic hormones to the tissue adjacent to and surrounding the eyeball.

DESCRIPTION OF THE RELATED ART

Dry eye, keratoconjunctivitis sicca, is the most common treatable eye disease in the United States. An estimated 58 million Americans suffer from dry eye. Dry eye disease includes keratoconjunctivitis (KCS), age-related dry eye, Stevens-Johnson syndrome, Sjogren's syndrome, occular cicatrical pemphigoid, blepharitis, Riley-Day syndrome, and congenital alacrima. Dry eye disease can also be caused by nutritional disorders or deficiencies (including vitamins), pharmacologic side effects, eye stress and glandular and tissue destruction, environmental exposure to smog, smoke, excessively dry air, airborne particulates, autoimmune and other immunodeficient disorders, and comatose patients who are unable to blink.

Currently, the pharmaceutical treatment of dry eye disease is mostly limited to administration of artificial tears (saline solution) to temporarily rehydrate the eyes. However, relief is short-lived and frequent dosing is necessary. In addition, artificial tears often have contra-indications and incompatibility with soft contact lenses (Lemp Cornea 9 S48-550 (1990)). The use of phosphodiesterase inhibitors, such as 3-isobutyl-1-methylxanthine (IBMX) to stimulate tear secretion is disclosed in U.S. Pat. No. 4,753,945. The effectiveness of these phsphodiesterase inhibitors is currently being investigated (Gilbard, et al., Arch. Opthal, 109 1672–76 (1991) and 112:1614–16 (1994); idem, Inv. Opthal. Vis. Sci. 31:1381–88 (1990)). Stimulation of tear secretion by topical application of melanocyte stimulating hormones is described in U.S. Pat. No. 4,868,154.

In addition, a topical ophthalmic formulation of cyclosporine (Restasis) has been investigated as a treatment of immune-based dry eye disease (Stern et al., Adv. Exp. Med. Biol., 438:643–651 (1998)). Stimulation of ocular mucin secretion has also been demonstrated with hydroxyeicosatetraenoic acid derivatives (Yanni, et al., U.S. Pat. No. 5,696, 166), gefarnate (Nakamura et al., Exp. Eye Res., 65–569–574 (1997)). U.S. Pat. No. 5,900,407 and WO 98/34593 (Yerxa et al.) disclose a method of stimulating tear secretion from lacrimal tissue by administering to the eyes an effective amount of purinergic receptor agonists such as uridine 5'-triphosphate, cytidine 5'-triphosphate, adenosine 5'-triphosphate, dinucleotides, and their analogs. Jumblatt and Jumblatt (Exp. Eye Res. 67:341–346 (1998)) demonstrate the effects of adenine analogues on secretion of high molecular weight, mucin-like glycoprotein by conjunctival goblet cells.

Additionally, a method for increasing hydration and lubrication of lacrimal tissues has been suggested by Yerxa, U.S. Pat. No. 6,277,855 (hereby specifically incorporated by reference in its entirety). This method involves administering to the subject a nicotinic acetylcholine receptor agonist such as nicotine and its analogs, such as transmetanicotine in an effective amount to stimulate mucus secretion in the lacrimal system.

Various physiological abnormalities have been proposed for the cause of dry eye. These physiological abnormalities include lack of tear volume and deficiencies in the precorneal tear film. Dry eye, however, is not caused by lack of tear volume alone, but a deficiency of tear components that result in epithelial pathology and inflammation of the ocular surface. Androgens have been demonstrated to modulate the anatomy, physiology, and the immune system of the lacrimal gland in rats, rabbits, hamsters, and humans. Decreased lacrimal output has been observed during pregnancy, oral contraceptive use, and post-menopause. Testosterone levels correlate with tear production in menopausal women. Patients who report severe dry eye are more likely to have low testosterone levels. If a male rat is castrated, lacrimal output is diminished and androgen supplementation will reverse the decrease. The levels of androgens that protect the ocular surface from inflammation decrease with age. When the level is reduced as in menopause, ocular cells make more cytokines that attract T cells to the conjunctiva, producing surface damage and increased symptoms of dry eye disease.

Because of the ability of androgens to modulate the immune system of the lacrimal gland, Applicants were motivated to study the inclusion of androgens in eye drops. It was found that androgens were not very soluble in water and difficult to deliver as an eye drop. The application of an androgen to the eye in the form of an eye drop would burn, sting and cause discomfort.

BRIEF SUMMARY OF THE INVENTION

It has been surprisingly and unexpectedly discovered that transdermal delivery of androgenic hormones to the adnexa of the eye results in a method to increase contact lens wear. This method involves transdermally administering a composition to a subject in need of such treatment, the composition being made of a therapeutically effective amount of an androgenic hormone in a pharmaceutically effective carrier. Additionally, it has been discovered that transdermal delivery of androgenic hormones to the adnexa of the eye results in a method of treating dry eye disease.

DETAILED DESCRIPTION OF THE INVENTION

Figure 1:
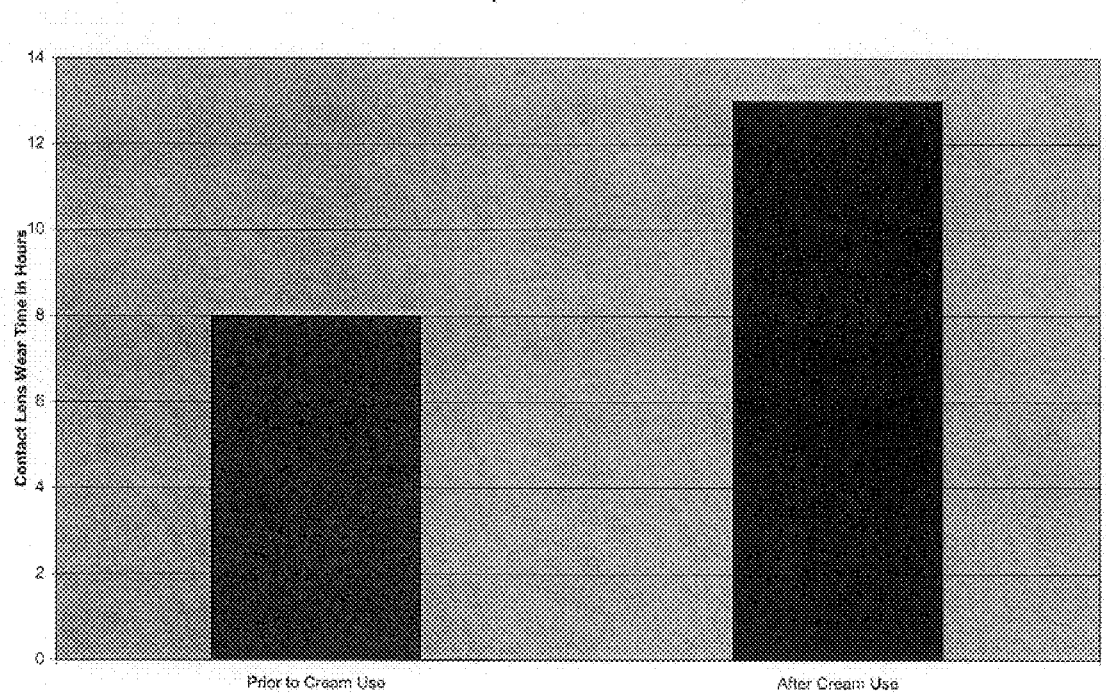
FIG. 1 shows the effect of androgenic cream on contact lens wear time.

This invention relates to a method for treating dry eye or increasing contact lens wear time through the transdermal delivery of androgenic hormones. More specifically, an androgenic hormone such as testosterone or dehydroepiandrosterone is solubilized in pharmaceutically effective carrier such as a facial cream or gel. The androgenic hormone in a pharmaceutically effective carrier is applied to the adnexa of the eye, which is the tissue adjacent to and surrounding the eyeball. The adnexa of the eye includes the eyelid, but is not limited to the eyelids.

This invention provides a method to increase contact lens wear time in subject. Referring to FIG. 1, the contact wear lens time is increased from an average of 8 hours to 13 hours after an androgenic hormone in a pharmaceutically acceptable carrier is applied to the adnexa of the eye. In the preferred embodiment, 2.5 weight % of dehydroepiandrosterone by weight of a facial cream is applied to the adnexa of the eye of a subject unable to wear contact lens for a normal period of time (i.e. greater than 12 hours). The cream is applied to the eyelid and on the eye lid margin twice daily. A small strip of cream is applied to the finger in the range of ¼ inch strip and the cream is massaged into the eyelid. After three days, contact lens wear increases to an average of 13 hours as shown in FIG. 1. Once a normal contact lens wear period is established, the subject will be able to resolve irritation or dryness in the eye within 30 minutes to 1 hour after the transdermal application of the androgenic hormone in a pharmaceutically acceptable carrier to the adnexa of the eye.

The invention also provides methods for treating dry eye diseases using transdermal delivery of androgenic hormones. Dihydrotestosterone effectively prevents degeneration and inflammation of the lacrimal gland and increases metabolic activity and tear secretion. This may be explained by the fact that androgens have an immunosuppressive effect through stimulating the synthesis of transforming growth factor, a potent immunomodulating and anti-inflammatory cytokine.

The pharmaceutical compositions useful in this invention are made of an androgenic hormone in a pharmaceutically acceptable carrier thereof. Useful compositions include a naturally occurring androgenic hormone such as testosterone or dehydroepiandrosterone or synthetic androgen hormones such as DHT (dihdrotestosterone), methandrostenoine, oxymetholone, ethylestrenol, oxandrolone, nandrolone phenpropionate, nandrolone decandate, stanozolol and dromostanolone propionate and a pharmaceutically effective carrier. The term "androgenic hormone" includes both natural and synthetic hormones. A pharmaceutically effective carrier includes: a gel or a cream.

A characteristic of the pharmaceutically effective carrier is that an androgenic hormone is sufficiently soluble to allow between 1 to 5% by weight of the androgenic hormone to be solubilized in a pharmaceutically acceptable carrier. Rosenbaum in U.S. Pat. No. 5,869,090 (hereby specifically incorporated by reference in its entirety) discloses transdermal delivery of dehydroepiandrosterone using phospholipids. A gel or a cream is used in the transdermal administration of the composition. In transdermal delivery, the skin serves as a reservoir for the sustained release of androgen into the systemic circulation. The amount of androgenic hormone that penetrates into the skin is (a) a function of the amount of pressure and vigor of rubbing, (b) surface area covered, (c) condition of the skin, (d) base used in the carrier and (e) use of occlusive dressings. Generally, 10% of the androgenic hormone applied transdermally is delivered to the subject.

The composition is applied to the adnexa of the eye of a subject in need of such treatment. The adnexa is the tissue adjacent to and surrounding the eyeball. The cream or gel is applied to eyelids and on the eye lids up to the eyelid margin. The composition is applied twice daily. A small strip of cream or gel is applied to the finger in the range of ¼ inch strip and the cream or gel is massaged onto the eyelid. The process is repeated for the second eye. In the preferred embodiment, the cream is applied twice daily. A subject, however, can add more treatment if he or she does not feel more comfortable.

Suitable pharmaceutically effective carriers for use with the formulations of the invention are well known in the cosmetic and pharmaceutical arts, and include such vehicles (or vehicle components) as water; organic solvents such as alcohols (particularly lower alcohols readily capable of evaporating form the skin such as ethanol), glycols (such as glycerin), aliphatic alcohols (such as alonolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes, protein-based materials such as collagen and gelatin; silicon-based materials (both non-volatile and volatile) such as cyclomethicone, demethiconol and dimethicone copolyol (Dow Coming); hydrocarbon-based materials such as petrolatum and squalane; anionic, cationic and amphoteric surfactants; sustained-release vehicles such as microsponges and polymer matrices; stabilizing and suspending agents; emulsifying agents, and other vehicles and vehicle components that are suitable for administration to the skin, as well as mixtures of topical vehicle components as identified above or otherwise known to the art. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in such reference works as *Martindale—The Extra Pharmacopoeia* (Pharmaceutical Press, London 1993) and Martin (ed.), *Remington's Pharmaceutical Sciences*.

Methodologies and materials for preparing formulations in a variety of forms are also describe in Anthony L. L. Hunting (ed.) "A Formulary of Cosmetic Preparations (Vol. 2)—Creams Lotions and Milks." Michelle press (England N.J. 1993). See, for example, Chapter 7, pp. 5–14 (oils and gels); Chapter 8, pp. 15–98 (bases and emulsions); Chapter 9, pp. 101–120 ("all-purpose products"); Chapter 10, pp. 121–124 (cleansing masks, creams, lotions); Chapter 11, pp. 185–208 (foundation, vanishing and day creams); Chapter 12, pp. 209–254 (emollients); Chapter 13, pp. 297–324 (facial treatment products); Chapter 14, pp. 325–380 (hand products); Chapter 15, pp. 461–484 (baby products); the contents of which are incorporated herein by reference.

Examples of useful gel are AndroGel® (United Pharmaceuticals, Deerfield Ill.) and Pluronic F-127NF (BASF Corporation, Mount Olive, N.J.). AndroGel® (United Pharmaceuticals, Deerfield Ill.) is a clear colorless hydroalcoholic gel containing 1% testosterone. AndroGel® provides continuous transdermal delivery of testosterone for 24 hours following a single application to the skin. Androgel® 1%, according to the package insert, is used as a topical preparation for the treatment of AIDS-related wasting syndrome and for men who low circulating levels of testosterone. AndroGel® is supplied in unit-dose aluminum foil packets in cartons of 30. Each packet contains 2.5 g or 5.0 g of gel to deliver 25 mg or 50 mg of testosterone, respectively.

A cream is an opaque, soft solids or thick liquids intended for external application consisting of medicaments dissolved or suspended in water soluble or vanishing cream bases. The term "cream" is applied to soft, cosmetically acceptable types of preparations. An example of a cream is a facial cream. A facial cream used to solubilize androgenic hormones can include purified water, white petrolatum, cetearyl alcohol and ceteareth-20, sorbitol solution, propylene glycol, simethicone, glyceryl monostearate, polyethylene glycol monostearate, sorbic acid and BHT. A facial cream can also be made of a mixture of paraffin oil, polyoxyethylene glycol 100 stearate, poloxyethylene glycol 100 monostearate, acetyl alcohol, monostearate, glycerol monostearate, triethanolamine, stearic acid and alpha-tocopherol. The composition may include lecithin to enhance the penetration of the androgenic hormones into the skin, as disclosed by Fawzi, U.S. Pat. No. 4,783,450 (hereby specifically incorporated by reference in its entirety).

Various creams have been used to solubilize androgenic hormones. These include testosterone cream was describe by Allen LV ("Testosterone propionate" US Pharmacist, April 1992, pp. 68–72 [hereby specifically incorporated by reference in it entirety]). Several formulations were presented, using testosterone propionate USP (powder) as the active ingredient. Two are repeated here:

| 1. Testosterone propionate | 1% |
|---|---|
| Hydrophilic petrolatum p.s. (Aquabase or Aquaphor) | 30 gm. |

Method: Levigate the powder into the base using geometric technique and a few drops of mineral oil or a small amount of the base as a levigating agent.

| 2. Testosterone propionate | 2 gm |
|---|---|
| Peanut oil | 20 ml |
| Water | 8 mL |
| Hydrophilic Ointment q.s. | 100 gm |

Method: Dissolve the testosterone propionate in the peanut oil. Add the hydrophilic ointment (Dermabase, Velvachol, etc.) with gentle heat until melted, add the water, mix and cool.

EXAMPLES (MATERIAL AND METHOD SECTION)

Example 1

A 49 year old Caucasian female who presented with dry burning eyes and eye strain. A diagnosis of dry eye was established, her tear breakup time (TBUT) was 1 sec right eye (OD) and 2 sec left eye (OS) Schirmer test was 11 mm OD and 5 mm OS. TBUT (tear breakup time) is a less accurate test for dry eye, as it looks at the stability of tear film. A normal TBUT is 10 seconds. This test is influenced by evaporation of the tears as well as tear production. If a patient has a TBUT of less than 10 seconds, they are though to have dry eye, but the dry is not necessarily the result of reduced tear secretion. Schirmer test measures tear production. A normal patient will wet a Schirmer strip 10 mm in 5 minutes. If it is less than 10 mm in 5 minutes, the patient is said to have dry eye. This means the patient does not secrete adequate tears. The patient had 2+ staining with Lissamine green in both eyes. After 2 weeks on a 2.5% by weight testosterone in a facial cream (facial cream, People's Custom Rx, Memphis, Tenn.) applied twice daily to her eyelids, she reported symptom relief increased contact lens wearing time. Her TBUT increased to 7 sec OD and 6 sec OS the Schirmer increased to 11 mm OD and 8 mm OS. She reported the cream started to provide relief within 30 minutes of application and the relief lasted several hours. She stated the cream reduced her symptoms a great deal. She said the composition allowed her to awaken with tears. She has used the product successfully since October, 2001. She also reports cosmetic benefit to the cream she said she and friends noticed her eyes look younger.

Example 2

A 29 year old Caucasian female who was unable to wear contact lenses with TBUT of 4 sec in each eye and a normal Schirmer test. She found applying 2.5% by weight DHEA in a facial cream (facial cream, People's Custom Rx, Memphis, Tenn.) twice a day to her eyelids increased her contact lens wear time from 2 hours a day to 11 hours a day. She did not show a significant change in TBUT or Schirmer test with the cream. She got relief from the cream within 1 hour of application and said the relief lasted all day. She said the cream reduced her eye ache. She has been using the cream since October 2001. She and friends have commented the cream made her eyes look less puffy.

Example 3

A 26 yr old Caucasian female with dry eye symptoms but a normal Schirmer test reported no relief of symptoms but felt her eyelids looked and felt better. She would like to use the 2.5% by weight DHEA in a facial cream (facial cream, People's Custom Rx, Memphis, Tenn.) as a cosmetic.

Example 4

A 31 year old Caucasian female was unable to wear contact lenses and increased her wear time by use of the 2.5% by weight DHEA in a facial cream (facial cream, People's Custom Rx, Memphis, Tenn.).

Example 5

A 33 year old Caucasian male has reduced TBUT 4 sec OD and 3 sec Os and Schirmer 2 mm OD and 3 mm OS. After 2 weeks of applying 2.5% by weight DHEA in a facial cream (facial cream, People's Custom Rx, Memphis, Tenn.) it 3 times a day to her eyelids, his TBUT improved to 4 sec OD and 5 sec OS and Schirmer improved to 4 mm OD and 7 mm OS. He felt his eyes were still dry but the scratchy feeling was lessened his relief lasted several hours and started within 30 minutes of application.

Example 6

A 25 yr old Caucasian female TBUT 2 sec both eyes Schirmer 11 mm OD and 14 mm OS. After two weeks of applying 2.5% by weight testosterone in a facial cream (Varicream®, Pharmaceutical Specialties, Inc., Rochester, Minn.) to her eyelids her TBUT was 6 sec OD and 4 sec OS with a Schirmer of 15 mm OD and 20 mm OS. She reported relief within one hour of application and the relief lasted for several hours.

Example 7

A 50 yr old Caucasian female with reduced TBUT but normal Schirmer test reported relief from 2.5% by weight DHEA in a facial cream (facial cream, People's Custom Rx, Memphis, Tenn.) for several hours and within 1 hour of application but no change in TBUT and Schirmer were observed.

Example 8

A 64 yr old Caucasian female with a history of Sjögren's syndrome presented with bilateral recurrent corneal erosions. She was treated with bilateral bandage contact lenses , Muro 128 5% qid (four times a day), Celluvisc qhs (at the hours of sleep or bedtime), artificial tears pm (as needed), tobramycin qid (four times a day) and AndroGel® 1% applied to the upper eyelids twice daily. She was seen back in three days at that time she reported vast improvement in comfort, her eyes were no longer sticking together as they were prior to treatment. At this visit we discontinued the bandage contact lenses and the tobramycin but continued the AndroGel®, Muro 128 and Celluvisc. This subject has been asymptomatic for one year and she reports her eyes have never felt better. The subject has not had a recurrent corneal erosion in one year. Supplementation with this hormone clearly improved this subject's dry eye symptoms, she had a visible tear meniscus as well as reduced conjunctival redness. The increased moisture in the eye also reduced the number of recurrent corneal erosion episodes from weekly to none in one year.

Example 9

A subject presented with bilateral ocular pain that began at three AM that morning. She had history of Sjögren's syndrome, as well as recurrent corneal erosions her lower lid puncta (drainage holes for tears in the eyelid) were plugged and she was taking Salagen(pilocarpine) to improve salivary secretion. The treatment she received for this recurrent red eye condition from a local ophthalmologist was tobradex qid (4 times a day) but after seven days of treatment the condition persisted so she presented to our clinic. Diagnostic Data: Best corrected visual acuities with spectacles OD 20/25 OS 20/20-2 Refractive data OD+2.75/OS+4.00 with a +2.25 add The K's (keratometry reading which measures the shape of the cornea) were spherical at 44.25 Biomicroscopy revealed SPK (superficial punctate keratitis (corneal irritation)) 2+ with epithelial defects OU (both eyes). Mild neovascularization was present mostly inferior. Mild conjunctival injection was present OU (both eyes). Anterior chamber was clear and the angles were open. IOP (intraoccular pressure) was 14 OD and 16 OS by NCT (non-contact tonometry a test of IOP used in glaucoma diagnosis). A dilated fundus exam was normal with C/D (cup-to-disk ratio for optical nerve head of the retina) ratio 0.25/0.25 in both eyes. Diagnosis: Based on the history and staining pattern a diagnosis of bilateral recurrent corneal erosions was established secondary to dry eye from Sjögren's syndrome. Treatment: Bandage contact lenses were prescribed to promote healing of the erosions. Muro 128 5% was added qid (four times a day) to remove excess fluid from the ocular surface to promote epithelial adhesion to the underlying extracellular matrix. Tobramycin qid (four times a day) was included prophylactically protect the epithelial defects against infection. Celluvisc qhs (at the hour of sleep or bedtime) was used because of its viscosity to minimize lid adherence from lack of moisture overnight. Artificial tears were added to increase ocular lubrication. AndroGel® 1% was prescribed to stimulate lacrimal gland secretion and improve meibomian gland function. Androge® 1% was applied to the adnexa of the eye. The subject returned three days later for a progress check her recurrent corneal erosions had resolved she reported her eyes were more comfortable and less injected. A tear meniscus was also noted that was not present on the initial exam. At this point we discontinued the bandage contact lenses and tobramycin. Based on her ocular improvement we corrected her in monovision contact lenses. We continued the AndroGel® twice daily applied to the upper eyelid region. One year after treatment she has not had any adverse incidents from the AndroGel®, she is able to wear contact lenses successfully and she has not experienced any recurrent corneal erosion episodes.

Although the present invention has been described and illustrated with respect to preferred embodiments and preferred uses thereof, it is not so limited since modifications and changes can be made therein which are within the full scope of the invention. The invention is therefore not limited to specific preferred embodiments as described, but is only limited as defined by the following claims.

I claim:
1. A method of treating dry eye disease comprising:
(a) transdermally administering a composition to a subject in need of such treatment, said composition comprising a therapeutically effective amount of an androgenic hormone in a pharmaceutically effective carrier wherein said transdermally administering involves administering said compound to the adnexa of the eye of said subject and said androgenic hormone comprised between 1 to 5% by weight of said pharmaceutically effective carrier.

2. The method of claim 1 wherein said pharmaceutically effective carrier is a cream.

3. The method of claim 1 wherein said pharmaceutically effective carrier is a gel.

4. The method of claim 1 wherein said androgenic hormone is testosterone.

5. The method of claim 1 wherein said androgenic hormone is dehydroepiandrosterone.

6. The method of claim 2 wherein said cream comprises one or more of purified water, white petrolatum, cetearyl alcohol and ceteareth-20, sorbitol solution, propylene glycol, simethicone, glyceryl monostearate, polyethylene glycol monostearate, sorbic acid and BHT.

7. The method of claim 2 wherein said androgenic hormone is dehydroepiandrosterone and dehdroepiandrosterone comprises between 1 to 5% by weight of said cream.

8. A method to increase contact lens wear time comprising:
(a) transdermally administering a composition to a subject in need of such treatment, said composition comprising a therapeutically effective amount of an androgenic hormone in a pharmaceutically effective carrier, wherein said transdermally administering involves applying said compound to the adnexa of the eye of said subject.

9. The method of claim 8 wherein said pharmaceutically effective carrier is a cream.

10. The method of claim 8 wherein said pharmaceutically effective carrier is a gel.

11. The method of claim 8 wherein said androgenic hormone comprised between 1 to 5% by weight of said pharmaceutically effective carrier.

12. The method of claim 8 wherein said androgenic hormone is testosterone.

13. The method of claim 8 wherein said androgenic hormone is dehydroepiandrosterone.

14. The method of claim 9 wherein said cream is comprised of purified water, white petrolatum, cetearyl alcohol and ceteareth-20, sorbitol solution, propylene glycol, simethicone, glyceryl monostearate, polyethylene glycol monostearate, sorbic acid and BHT.

15. The method of claim 9 wherein said cream comprises one or more of purified water, white petrolatum, cetearyl alcohol and ceteareth-20, sorbitol solution, propylene glycol, simethicone, glyceryl monostearate, polyethylene glycol monostearate, sorbic acid and BHT.

* * * * *

UNITED STATES PATENT AND TRADEMARK OFFICE
CERTIFICATE OF CORRECTION

PATENT NO.     : 6,659,985 B2
DATED          : December 9, 2003
INVENTOR(S)    : Conner It is certified that error appears in the above-identified patent and that said Letters Patent is hereby corrected as shown below:

Title page,
Item [75], -- Charles L. Haine, Memphis TN -- is added as an inventor.

Signed and Sealed this

Sixteenth Day of March, 2004

JON W. DUDAS
*Acting Director of the United States Patent and Trademark Office*